United States Patent [19]

Himmelstrup

[11] Patent Number: 4,475,905
[45] Date of Patent: Oct. 9, 1984

[54] INJECTION DEVICE

[76] Inventor: Anders B. Himmelstrup, 1333 Chelmsford St., St. Paul, Minn. 55108

[21] Appl. No.: 429,968

[22] Filed: Sep. 30, 1982

[51] Int. Cl.³ .............................................. A61M 5/00
[52] U.S. Cl. .................................... 604/208; 604/263
[58] Field of Search ............... 604/192, 218, 197, 198, 604/210, 157, 224, 263, 207, 208, 210, 407

[56] References Cited

U.S. PATENT DOCUMENTS

| | | | |
|---|---|---|---|
| 2,117,469 | 5/1938 | Woodyatt | 604/197 |
| 2,347,179 | 4/1944 | Gorman | 604/157 |
| 2,400,722 | 5/1946 | Swan | 604/192 |
| 2,460,039 | 1/1949 | Scherer et al. | 128/218 |
| 2,472,116 | 6/1949 | Maynes | 604/224 |
| 2,739,591 | 3/1956 | Yochem | 128/218 |
| 2,847,996 | 8/1958 | Cohen et al. | 604/192 |
| 3,677,246 | 7/1972 | Stein | 128/218 |
| 3,688,765 | 9/1972 | Gasaway | 128/173 |
| 3,712,301 | 1/1973 | Sarnoff | 128/218 |
| 3,720,211 | 3/1973 | Kyrias | 128/218 |
| 3,780,734 | 12/1973 | Wolff | 604/197 |
| 3,943,927 | 3/1976 | Norgren | 604/197 |
| 4,050,459 | 9/1977 | Sanchez | 604/210 |
| 4,170,993 | 10/1979 | Alvarez | 604/263 |
| 4,346,708 | 8/1982 | Leveen et al. | 128/236 |

OTHER PUBLICATIONS

"Diabetes Care," a Publication of The American Diabetes Association, Inc., vol. 5, No. 3, May/Jun. 1982.

Primary Examiner—John D. Yasko
Attorney, Agent, or Firm—Kinney & Lange

[57] ABSTRACT

An injection device delivers a preselected dose of a drug, such as insulin, from a conventional syringe. The device includes a sleeve having a first opening and a cavity sufficiently large to house a barrel of a conventional syringe. The sleeve further includes a second opening through which a cannula of the syringe extends and which is sufficiently small to retain the barrel of the syringe. A plunger-engaging cap is positioned within the sleeve in sliding relationship and engages a plunger of the syringe. The sleeve includes a slot preferably extending longitudinally along the sleeve and the plunger-engaging cap includes a pin extending outwardly from the cap's surface and positioned within the slot. A stop is positionable at a predetermined location along the slot defining a preselected dosage such that when the plunger-engaging cap is pushed into the sleeve, the plunger of the syringe is pushed within the barrel of the syringe with the cap and plunger stopping when the pin of the cap engages the stop thereby expelling the preselected dose of the drug.

5 Claims, 5 Drawing Figures

INJECTION DEVICE

BACKGROUND OF THE INVENTION

1. Field of the Invention

The present invention relates to injection devices, and in particular, it relates to an injection device that uses a conventional syringe in delivering one or more preselected doses of a drug.

2. Description of the Prior Art

Daily self-administered hypodermic injections are a common form of drug administration for many persons suffering from diseases such as diabetes. In the case of a diabetic, insulin is administered on a daily schedule which is designed to correspond to high levels of glucose within the cardio-vascular system. The schedule of administration of insulin varies among diabetics according to the needs of the diabetic and the type of insulin being used.

There are basically three types of insulin: short-acting, intermediate-acting, and long-acting insulin. The most commonly used insulins are Regular and Lente (short-acting insulins) and NPH (intermediate-acting insulin). Intermediate and long-acting insulins are administered once or twice a day. The short-acting insulins are normally administered at mealtimes to counter high levels of glucose associated with meals. Normally, the dosage of, for example, Lente insulin is a rather small dosage ranging from 0.3 to 0.4 c.c. before a meal.

However, the injection of insulin at every meal is quite an inconvenience, especially when dining out. It is crucial to many diabetics to take a dose of regular insulin at each mealtime. However, because of the inconvenience, most diabetics do not take the injection and maintain dangerously high glucose levels. For each injection, alcohol, a bottle of insulin and a syringe is needed. The area of the body where the injection is to be made needs to be cleansed with alcohol and then the syringe must be loaded with insulin from the bottle. When the injection is made, in the case of a disposable syringe, the syringe is thrown away after only one injection of a small amount of insulin. When a nondisposable syringe is used, the syringe needs to be cleaned prior to being used again. In either case, it is very inconvenient to prepare for the injection, administer the injection, and in the case of a nondisposable syringe, to clean the syringe afterwards.

There have been several attempts in the prior art to make the injection process more convenient and to ensure that the amount of the dosage for each injection is precise.

In the Yochem U.S. Pat. No. 2,739,591, a device which is attached to a syringe permits the user to administer successive uniform injections. The device is used in a situation where a technician or physician is administering the same uniform dosage to a number of people. However, the device does not permit a single user to conveniently self-administer insulin from one mealtime to the next. First, no provision is made for the needle to be kept sterile between injections. Second, considerable care must be taken in carrying a loaded syringe so that the syringe is not accidentally actuated.

The Kyrias U.S. Pat. No. 3,720,211 describes a device that manipulates a hypodermic syringe to automatically administer an injection. However, the device of the Kyrias Patent expells the entire charge within the syringe and is useful for only one injection.

The Stein U.S. Pat. No. 3,677,246 shows a hypodermic syringe having a relatively small injection chamber with an adjustable volume and with a second relatively larger supply chamber which is adapted to hold a relatively large supply of injection solution. The smaller injection chamber is connected to the larger supply chamber and a pump is associated with the supply chamber, operable by a plunger from outside the syringe, to supply injection solution to the injection chamber. This type of syringe has the disadvantage of being complex in construction and expensive to manufacture.

Other patents, the Gasaway U.S. Pat. No. 3,688,765, the Scherer et al U.S. Pat. No. 2,460,039, the Wallin U.S. Pat. No. 2,373,520 and the Sarnoff U.S. Pat. No. 3,712,301, describe other devices for use in injecting solutions. However, none of these devices are sufficiently practical and convenient for an insulin administration schedule.

SUMMARY OF THE INVENTION

The present invention includes a device which uses a standard hypodermic syringe. The syringe is fully loaded with a drug, such as insulin, and placed within the device. The device keeps the needle of the insulin sterile and is sufficiently compact to be carried in a pocket. Multiple preselected dosages are administered using the device until the syringe is empty.

The device includes a sleeve having a first opening and a cavity sufficiently large to house the syringe and a second opening sufficiently small to retain the syringe while permitting the cannula to extend therethrough. A plunger-engaging cap is insertable within the first opening and cavity of the sleeve. The cap has a first open end and a cavity for housing the plunger and a second closed end for engaging the plunger of the syringe. The cap further includes a pin that slides within a slot of the sleeve. A stop is located on the sleeve a predetermined distance from the pin defining a preselected dose of the drug. To expel the preselected dose, the plunger cap is pushed within the sleeve to push the plunger of the syringe until the pin engages the stop. In one embodiment, the stop is a stop movable along the sleeve and the sleeve contains indicia which indicate the amount of dosage being expelled from the syringe.

DETAILED DESCRIPTION OF THE PREFERRED EMBODIMENT

Figure 1:
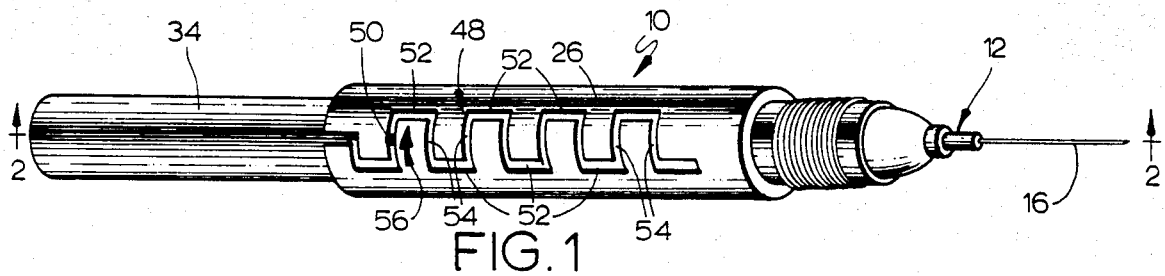
FIG. 1 is a perspective view of the device of the present invention with a standard hypodermic syringe.
Figure 2:
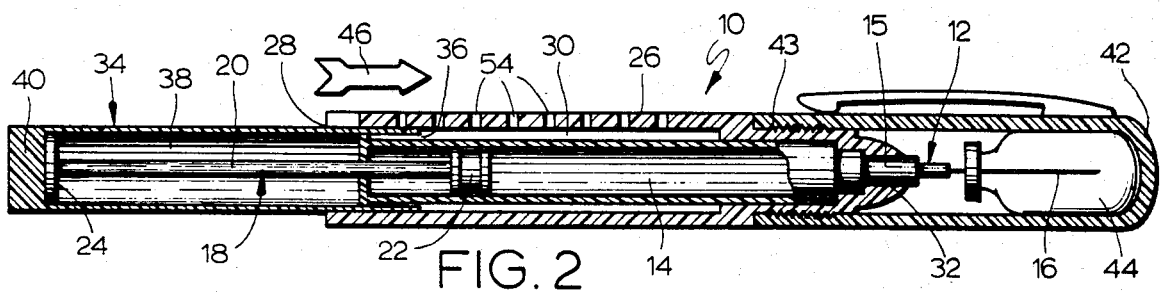
FIG. 2 is a cross sectional view of the device and a hypodermic syringe taken along line 2—2 in FIG. 1.

The device of the present invention is generally indicated at 10 in FIGS. 1 and 2. The device 10 houses a standard syringe 12. The syringe 12, best shown in FIG. 2, is a standard-type syringe and includes a barrel 14 for holding injection solution, a cannula 16 attached to one end of the barrel and communicating with the interior thereof, and a plunger 18. The plunger 18 includes a plunger shaft 20 with a piston 22, commonly referred to in a syringe as a stopper, frictionally engaging the inside surface of the barrel 14 and a collar 24, which is normally a thumb rest, for pushing the stopper through the barrel 14 and expelling solution from within the barrel.

The device 10 includes a sleeve 26 having an opening 28 at one end through which the syringe 12 is inserted into a cavity 30. The sleeve 26 also includes a second opening 32 through which the cannula 16 of the syringe extends. The opening 32 is of a size that allows a cannula hub 15 to extend through while retaining the barrel 14 of the syringe 12 within the cavity 30. The hub 15 supports the cannula 16. Where the cannula extends directly from the barrel rather than from a cannula hub, the the opening 32 would be a size comparable to the size of the cannula 16.

Figure 3:
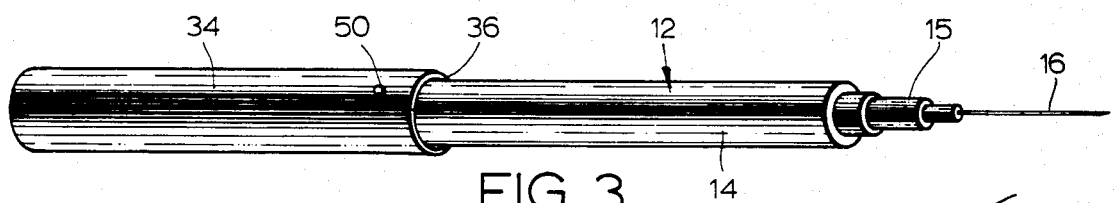
FIG. 3 is a perspective view of the plunger-engaging cap and hypodermic syringe with the sleeve having been removed.

A plunger-engaging cap 34 is insertable within the sleeve 26, as best seen in FIGS. 1 and 2. The plunger-engaging cap 34 has an open end 36 for receiving the plunger 18 and a rearward portion of the barrel 14 within a cavity 38, as best seen in FIGS. 2 and 3. The cap 34 also has a plunger-engaging end 40 which engages the collar 24 of the plunger 18. The cap 34 slidably engages the inside surface of the cavity 30 of the sleeve 26.

Between injections, the cannula 16 must be kept sterile. An outer cap 42 is configured to receive the cannula 16 and a bottle 44 of sterilized solution. The cap 42 preferably attaches to an outer surface of the sleeve 26. As shown in FIG. 2, the cap 42 is in threaded engagement at 43 with the sleeve 26. However, other suitable types of arrangements are within the scope of the invention, such as a snap-fit.

To keep the cannula 16 sterile, preferably a sealed bottle 44 having a sterilizing solution, such as alcohol, is fitted within the cap 42. The bottle 44 has a top with a resealable membrane that is penetrable by the cannula and that seals the bottle each time the cannula is withdrawn. When the cap 42 is attached to the sleeve 26, the cannula enters the sterile interior of the bottle 44. It should be understood that other types of sterilizing devices such as a solution retaining fibrous material such as cotton that will keep the cannula sterile while stored within the interior of the cap 42 are within the scope of the present invention.

The sleeve 26, the plunger-engaging cap 34 and the outer cap 34 are made of rigid material such as metal or plastic. The material is preferably non-corrosive and easily kept clean.

The device 10 further includes a mechanism wherein the preselected dosage is automatically expelled from the syringe by pushing the cap 34 into the sleeve 26 in a direction of arrow 46. In the embodiment shown in FIGS. 1 and 4, the mechanism includes a step-like configured slot 48 running longitudinally along the sleeve 26. A pin 50 is attached to an outside surface of the cap 34 and slidably communicates with the slot 48. The step-like configured slot 48 has longitudinally-running staggered slot portions 52 which define a predetermined number of units of a drug, such as insulin, within the barrel of the syringe 12. Between each staggered slot portion 52 and communicating with two staggered slot portions, is a transverse slot portion 54. The space between transverse slot portions 54 defines the length of each staggered slot portion 52.

To use the device of the present invention, a syringe 12 is fully loaded with a drug such as insulin. In a typical example, a popular size of insulin syringe carries 0.5 c.c. what is more commonly referred to as 50 units. The syringe is loaded in the usual manner wherein the cannula is inserted into a bottle of insulin and the plunger fully dranw, filling the barrel with insulin. All air bubbles are removed from the barrel in a conventional manner to ensure an accurate amount of insulin is in the syringe. When the syringe is fully loaded, it is inserted within the sleeve and the cap 34 is placed over the plunger 18 and a rearward portion of the barrel 14 of the syringe. The pin 50 is then positioned within the slot and is moved transversely as indicated by arrow 56 in FIG. 1 until the pin slides into a staggered slot portion 52. When the pin is in the staggered slot portion 52, the device is ready to expell a predetermined amount of insulin from the syringe.

Figure 4:
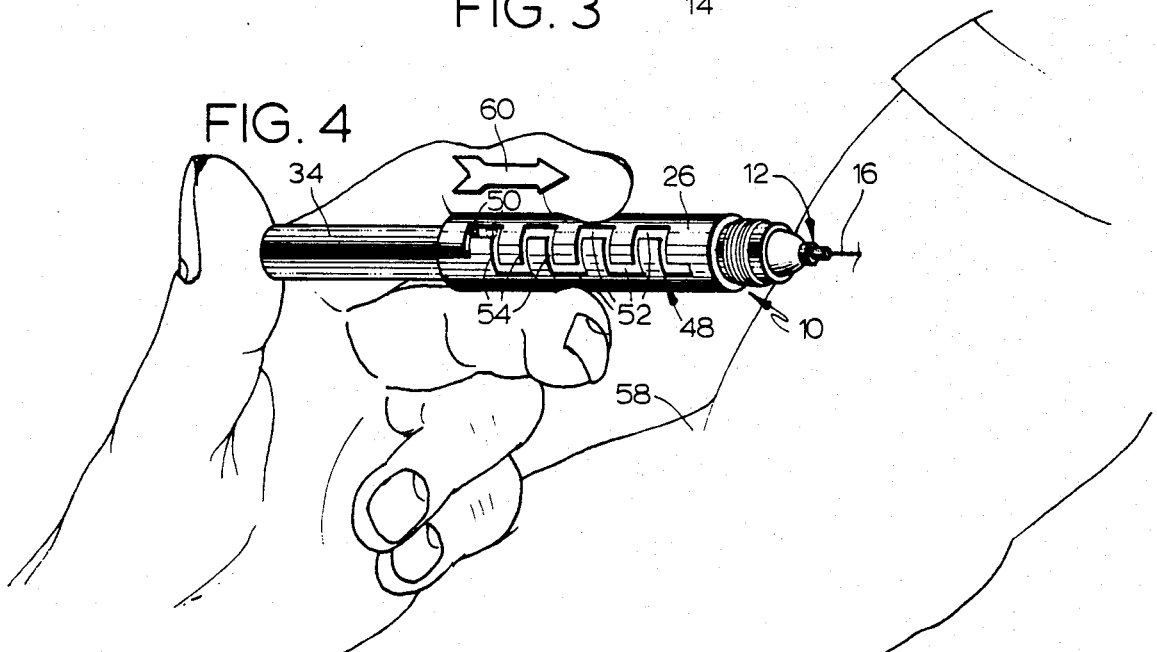
FIG. 4 is a perspective view of the device of the present invention in use.

As illustrated in FIG. 4, the device is used in a manner similar to using a regular syringe. The cannula 16 is inserted within the skin 58 of the user and the cap 34 is manually pushed in into the sleeve 26. The pin 50 moves in the direction of arrow 60 until it engages a transverse slot portion 54 as indicated by the pin 50 in phantom. As is easily understood from the above, with the staggered slot portion 52 defining a predetermined amount of insulin such as 3 units the device 10 automatically delivers the 3 units of insulin to the user.

When the injection has been completed, the cap 42 is placed over the cannula with the cannula 16 being inserted within the sterile environment of the bottle 44. The device 10 is then stored, for example, in a pocket for use in administering another subsequent injection using the same syringe. When the next injection is needed, the cap 42 is disengaged from the sleeve 26 with the sterile cannula being automatically removed from the bottle 44. The plunger-engaging cap 34 is then rotated again moving the pin 50 along a transverse slot portion 54 until the next staggered slot portion 52 is engaged. The same procedure as described above is once again followed to inject a predetermined amount of insulin into the user.

Figure 5:
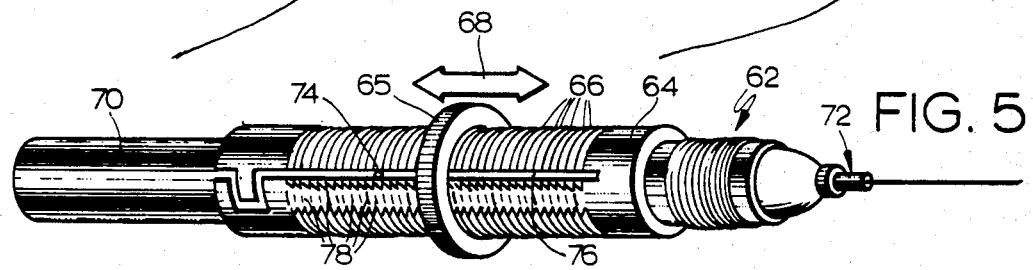
FIG. 5 is a perspective view of a preferred embodiment of the present invention having an adjustable stopper.

In another embodiment of the present invention genrally indicated at 62 in FIG. 5, a sleeve 64 similar to the sleeve 26 includes a plurality of outer threads 66. A ring 65 threadably engages the threads 66 and moves longitudinally along the sleeve 64 in a direction of arrow 68 as the ring 65 is rotated on the threads 66. A plunger-engaging cap 70 similar to the cap 34 is also positioned within the sleeve 64 and over a plunger and barrel (not shown) of a syringe 72. The cap 70 also contains a pin 74 which slidably communicates with a linear slot 76 running longitudinally along the sleeve 64. The pin 74 extends through the slot 76 sufficiently to engage the ring 65 as a stop. Positioned along the sides of the sleeves are indicia 78 which correspond to units of a drug within the syringe 72.

The embodiment shown in FIG. 5, permits the user to preselect any desired amount of insulin to be expelled from the syringe 72. The user simply moves the ring 65 along the sleeve 64 until the desired amount of units lie between the pin 74 and the ring 65 as indicated by the indicia 78. When the ring 65 is set in the preselected position, the cap 70 is similarly engaged, as illustrated in FIG. 4, and the desired amount of insulin is expelled from the syringe 72 into the user.

CONCLUSION

The device of the present invention holds a fully-loaded syringe and the cannula of the syringe in a sterile environment ready for use. The device is compact and can be carried with the user in a pocket. The device delivers a preselected dosage to the user and permits use of the same syringe for several dosages.

Although the present invention has been described with reference to preferred embodiments, workers skilled in the art will recognize that changes may be made in form and detail without departing from the spirit and scope of the invention.

What is claimed is:

1. A device for delivering a plurality of preselected doses of a drug from a loaded syringe having a plunger at a first end and a cannula at a second end, the device comprising:

a sleeve having a first opening and a cavity sufficiently large to house the syringe and a second opening sufficiently small to retain the syringe while permitting the cannula to extend therethrough and a slotted track having a plurality of staggered longitudinally positions slot portions and transversely positioned slot portions with each transversely positioned slot portion communicating with two longitudinally positioned slot portions;

a plunger-engaging cap telescopically movable within the sleeve and having a first open end and a plunger cavity for housing the plunger and a second closed end for engaging an end of the plunger and an outwardly extending pin for following the track, placing the sleeve and the plunger cap in a cooperating relationship so that when the syringe is loaded only a single preselected dose of the drug is injectable through the cannula when the plunger cap is pushed inwardly into the cavity of the sleeve the pin follows a longitudinal slot and stops at a transverse slot leaving any remaining amount of the drug within the syringe and placing the sleeve and plunger cap in subsequent cooperation for delivering subsequent preselected doses from the same syringe by moving the pin along the transverse slot until the pin enters a next longitudinal slot.

2. The device of claim 1 and further including: means for keeping the cannula sterile detachably attachable over the second opening of the sleeve.

3. The device of claim 2 wherein the means for keeping the cannula sterile is a cap having means for holding a sterilizing drug.

4. The device of claim 3 wherein the means for holding a sterilizing drug includes a container holding the sterilizing drug having a membrane penetrable by the cannula.

5. A device for delivering a plurality of preselected doses of a drug from a loaded syringe having a plunger at a first end and a cannula at a second end, the device comprising:

a sleeve having a first opening and a cavity sufficiently large to house the syringe and a second opening sufficiently small to retain the syringe while permitting the cannula to extend therethrough;

a plunger-engaging cap telescopically engaging the sleeve and having a first open end and a plunger cavity for housing the plunger and a second closed end for engaging an end of the plunger; and means for determining a plurality of preselected doses and for providing for a series of limited movements of the plunger includes a pin attached to a surface of the plunger cap and extending into a slot of the sleeve with the plunger cap slidably engaging the sleeve in a cooperating relationship and wherein the slot is linear and runs longitudinally along the sleeve and including a stop ring threadably engaging the exterior surface of the sleeve and movable longitudinally along the sleeve such that a predetermined dosage of the drug is injectable through the cannula when the plunger cap is pushed inwardly into the cavity of the sleeve.

* * * * *